(12) United States Patent
Greenberg et al.

(10) Patent No.: US 9,161,533 B2
(45) Date of Patent: *Oct. 20, 2015

(54) PLANT PATHOGEN RESISTANCE

(71) Applicants: The University of Chicago, Chicago, IL (US); UT-Battelle, LLC, Oak Ridge, TN (US)

(72) Inventors: Jean T. Greenberg, Chicago, IL (US); Ho Won Jung, Chicago, IL (US); Timothy Tschaplinski, Oak Ridge, TN (US)

(73) Assignees: The University of Chicago, Chicago, IL (US); UT-Battelle, Oak Ridge, TN (US)

( * ) Notice: Subject to any disclaimer, the term of this patent is extended or adjusted under 35 U.S.C. 154(b) by 50 days.

This patent is subject to a terminal disclaimer.

(21) Appl. No.: 13/657,557

(22) Filed: Oct. 22, 2012

(65) Prior Publication Data

US 2013/0130907 A1     May 23, 2013

Related U.S. Application Data

(63) Continuation of application No. 12/191,833, filed on Aug. 14, 2008, now Pat. No. 8,318,786.

(60) Provisional application No. 60/956,301, filed on Aug. 16, 2007.

(51) Int. Cl.
| A61K 31/425 | (2006.01) |
| A61K 31/19 | (2006.01) |
| A01N 37/04 | (2006.01) |
| C05G 3/02 | (2006.01) |

(52) U.S. Cl.
CPC . *A01N 37/04* (2013.01); *C05G 3/02* (2013.01)

(58) Field of Classification Search
None
See application file for complete search history.

(56) References Cited

U.S. PATENT DOCUMENTS

| 4,622,248 | A | 11/1986 | Leach et al. | 427/440 |
| 5,326,790 | A | 7/1994 | Thornfeldt | 514/784 |
| 5,514,374 | A | 5/1996 | Bonte et al. | 424/745 |
| 5,624,673 | A | 4/1997 | Bonte et al. | 424/745 |
| 5,653,983 | A | 8/1997 | Meybeck et al. | 424/745 |
| 5,679,374 | A | 10/1997 | Fanchon et al. | 424/450 |
| 6,190,664 | B1 | 2/2001 | Dampeirou | 424/736 |
| 6,419,935 | B1 | 7/2002 | Gueret | 424/401 |
| 6,482,839 | B1 | 11/2002 | Thornfeldt | 514/345 |
| 6,927,206 | B2 | 8/2005 | Patt | 514/2.4 |
| 6,979,454 | B1 | 12/2005 | Lindahl et al. | 424/409 |
| 2003/0198610 | A1 | 10/2003 | Nakayama et al. | 424/59 |
| 2003/0204983 | A1 | 11/2003 | Porter | 43/3 |
| 2004/0097372 | A1* | 5/2004 | Abraham et al. | 504/127 |
| 2004/0156873 | A1 | 8/2004 | Gupta | 424/401 |
| 2004/0175407 | A1 | 9/2004 | McDaniel | 424/423 |
| 2004/0254097 | A1 | 12/2004 | Patt | 514/6 |
| 2004/0258652 | A1 | 12/2004 | Pascaly et al. | 424/70.27 |
| 2005/0002887 | A1 | 1/2005 | Rollat-Corval et al. | 424/70.1 I |
| 2005/0074414 | A1 | 4/2005 | Tamarkin et al. | |
| 2005/0244360 | A1 | 11/2005 | Billoni | 424/70.22 |
| 2006/0018937 | A1 | 1/2006 | Friedman et al. | 424/401 |
| 2006/0062832 | A1 | 3/2006 | Lopes | 424/443 |
| 2006/0194699 | A1 | 8/2006 | Moucharafieh et al. | 504/206 |
| 2006/0233721 | A1 | 10/2006 | Tamarkin et al. | 424/47 |
| 2006/0269485 | A1 | 11/2006 | Friedman et al. | 424/45 |
| 2007/0020304 | A1 | 1/2007 | Tamarkin et al. | 424/403 |

FOREIGN PATENT DOCUMENTS

| EP | 0450087 | 10/1991 |
| EP | 582239 | 2/2004 |
| JP | 2003/522135 | 3/2003 |
| KR | 10-2002-0078155 | 10/2002 |
| KR | 10-2003-0069973 | 8/2003 |
| SU | 510 462 | 6/1976 |
| WO | WO 85/04668 | 10/1985 |
| WO | WO 94/06440 | 3/1994 |
| WO | WO 00/32048 | 6/2000 |
| WO | WO 01/19187 | 3/2001 |
| WO | WO 01/82869 | 11/2001 |
| WO | WO 02/072039 | 11/2002 |
| WO | WO 03/000243 | 1/2003 |
| WO | WO 2006/062835 | 6/2006 |

OTHER PUBLICATIONS

Cao et al., "Characterization of an Arabidopsis Mutant That Is non-responsive to Inducers of Systemic Acquired Resistance," Plant Cell, 6: 1583-1592 (1994).
Delaney et al. "A Central Role of Salicylic Acid in Plant Disease Resistance," Science, 266:1247-1250 (1994).
Feys et al., "Direct interaction between the Arabidopsis disease resistance signaling proteins, EDS1 and PAD4," The EMBO Journal, 20 (19): 5400-5411 (2001).
Gaffney et al., "Requirement of Salicylic Acid for the Induction Systemic Acquired Resistance," Science, 261: 754-756 (1993).
Glazebrook et al., "Isolation of Arabidopsis Mutants With Enhanced Disease Susceptibility by Direct Screening," Genetics, 143: 973-982 (1996).

(Continued)

*Primary Examiner* — Craig Ricci
(74) *Attorney, Agent, or Firm* — Norton Rose Fulbright US LLP

(57) ABSTRACT

Azelaic acid or its derivatives or analogs induce a robust and a speedier defense response against pathogens in plants. Azelaic acid treatment alone does not induce many of the known defense-related genes but activates a plant's defense signaling upon pathogen exposure.

19 Claims, 7 Drawing Sheets

(56) References Cited

OTHER PUBLICATIONS

Glazebrook et al., "Isolation of phytoalexin-deficient mutants of Arabidopsis thaliana and characterization of their interactions with bacterial pathogens," Proc. Nat/. Acad. Sci., 91:8955-8959 (1994).
Glazebrook et al., "Phytoalexin-Deficient Mutants of Arabidopsis Reveal That PAD4 Encodes a Regulatory Factor and That Four PAD Genes Contribute to Downy Mildew Resistance," Genetics, 146: 381-392 (1997).
Greenberg et al., "Identifying type III effectors of plant pathogens and analyzing their interaction with plant cells," Current 02]nion in Microbiology_., 6: 20-28 (2003).
Gupta et al., "Arabidopsis thaliana EDS4 Contributes to Salicylic Acid (SA)-Dependent Expression of Defense Responses: Evidence for Inhibition of Jasmonic Acid Signaling by SA," MPMI, 13: 503-511 (2000).
Heck et al., "Genetic evidence that expression of NahG modifies defence pathways independent of salicylic acid biosynthesis in the Arabidopsis-Pseudomonas syringae pv. tomato interaction," The Plant Journal, 36: 342-352 (20031.
International Search Report in PCT/US2008/073169 issued in 2009.
Kato et al., "Oxidized unsaturated fatty acids related to resistance to rice blast disease," *Kagaku to Seibutu. Chemistry and Biology*, 24:183-188, 1986. (English translation of Japanese publication).
Lu et al., "ACD6, a Novel Ankyrin Protein, is a Regulator and an Effector of Salicylic Acid Signaling in the Arabidopsis Defense Response," The Plant Cell, 15: 2408-2420 (2003).
Mauch-Mani et al., "Salicylic Acid and Systemic Acquired Resistance to Pathogen Attack," Annals of Botany, 82: 535-540 (1998).
Mayda et al., "Arabidopsis dth9 Mutation Identifies a Gene Involved in Regulating Disease Susceptibility without Affecting Salicylic Acid-Dependent Responses," The Plant Cell, 12:2119-2128 (2000).
Nagaoka et al., "Fungitoxic compounds from the roots of tomato stock," *Ann. Phytopathol. Soc. Jpn.*, 61:103-108, 1995.
Nawrath et al., "EDS5, an Essential Component of Salicylic Acid-Dependent Signaling for Disease Resistance in Arabidopsis, Is a Member of the MATE Transporter Family," The Plant Cell, 14: 275-286 (2002).
Nawrath et al., "Salicylic Acid Induction-Deficient Mutants of Arabidopsis Express PR-2 and PR-5 and Accumulate High Levels of Camalexin after Pathogen Inoculation," The Plant Cell, II: 1393-1404 (1999).
Rogers et al., "Arabidopsis Enhanced Disease Susceptibility Mutants Exhibit Enhanced Susceptibility to Several Bacterial Pathogens and Alterations in PR-I Gene Expression," The Plant Cell, 9: 305-316 (1997).
Shapiro et al., "The Role of NDR1 in Avirulence Gene-Directed Signaling and Control of Programmed Cell Death in Arabidopsis," Plant Physiol, 127: 1089-1101 (2001 ).
Supplementary European Search Report and European Search Opinion issued in European patent application No. 08843231.5 dated Jan. 23, 2012.
Tao et al., "Quantitative Nature of Arabidopsis Responses during Compatible and Incompatible Interactions with the Bacterial Pathogen Pseudomonas syringae," The Plant Cell, 15: 317-330 (2003).
van Wees et al., "Loss of non-host resistance of Arabidopsis NahG to Pseudomonas syringae pv. Phascolicola is due to degradation products of salicylic acid," The Plant Journal, 33: 733-742 (2003).
Wildermuth et al., "Isochorismate synthase is required to synthesize salicylic acid for plant defence," Nature, 414: 562-565 (2001 ).
Zhou et al., "PAD4 Functions Upstream from Salicylic Acid to Control Defense Responses in Arabidopsis," The Plant Cell, 10: 1021-1030 (1998).
Office Communication in U.S. Appl. No. 12/191,833 dated Apr. 16, 2010.
Applicant Response to Restriction Requirement in U.S. Appl. No. 12/191,833 dated Apr. 16, 2010 filed Aug. 16, 2010.
Office Communication in U.S. Appl. No. 12/191,833 dated Mar. 3, 2011.
Response to Non-Final Office Action dated Mar. 3, 2011 in U.S. Appl. No. 12/191,833, filed Aug. 3, 2011.
Office Communication in U.S. Appl. No. 12/191,833 dated Oct. 26, 2011.
Response to Final Rejections in U.S. Appl. No. 12/191,833 dated Oct. 26, 2011 filed Apr. 26, 2012.
Office Action in Australian Patent Application No. 2008317218 issued Dec. 19, 2012.
Maldonado et al., "A putative lipid transfer protein involved in systemic resistance signaling in Arabidopsis," *Nature* 419:399-403, Sep. 26, 2002.

\* cited by examiner

PLANT PATHOGEN RESISTANCE

This application is a continuing application of U.S. patent application Ser. No. 12/191,833 filed Aug. 14, 2008, which claims priority to U.S. Provisional Patent Application Ser. No. 60/956,301, filed Aug. 16, 2007, the contents of which are incorporated herein by reference in their entirety.

The United States Government has rights in this invention pursuant to Contract Number DE-AC05-00OR22725 between the U.S. Department of Energy and UT-Battelle, LLC and also pursuant to Contract Number IOB-0450207 awarded by the U.S. National Science Foundation.

BACKGROUND

Azelaic acid, derivatives and analogs thereof increase resistance to plant pathogens and prime plants to resist pathogen infection.

Plants activate both local and systemic defenses against many pathogens (virulent, avirulent and non-host) in responses that involve the induction of hundreds of genes. Thus, plants make a substantial investment in defense responses that help limit the growth of pathogens. Plant responses to many pathogens are often categorized as either compatible or incompatible, based on the degree of disease. In these two extremes, the pathogen typically either grows and causes extensive disease symptoms (the compatible case) or is relatively restricted in its replication (the incompatible case). In the case of incompatible responses (also called "resistance responses"), signaling is initiated by the perception of pathogen-derived Avirulence (Avr) proteins that interact directly or indirectly with cognate plant R proteins. Even in compatible interactions, it is now clear that the plant can often mount a defense response that is partially effective in limiting the pathogen. Global expression profiling after pathogen infection suggests that the compatible and incompatible responses largely affect the same sets of target genes, although the speed and degree to which they are induced is lower in the compatible case. A subset of these target genes is likely induced because it encodes important regulatory proteins that participate directly in signal transduction cascades or generates signal transduction intermediates. Understanding how these regulatory genes are activated under different conditions can give significant insight into signal flux through regulatory circuits.

The induction of salicylic acid (SA) synthesis is required for conferring resistance to a variety of compatible and incompatible pathogens. A number of mutants with reduced accumulation or signal transduction of SA also display increased susceptibility to pathogens like *Pseudomonas syringae*, a gram-negative extracellular pathogen.

In addition to being important for local defense responses, SA has been implicated in a whole-plant adaptive response to pathogens called systemic acquired resistance (SAR). After infection with an avirulent pathogen, SA accumulates in the systemic uninfected tissue. This systemic tissue shows increased resistance to many pathogens that would otherwise be highly virulent. Plants that cannot accumulate or perceive increased levels of SA in systemic tissues do not develop SAR. However, SA is thought not to be the key mobile defense signal in SAR and as yet unidentified signals generated during the defense response may also play a role in establishing SAR. Discovering the identity and properties of these unidentified signal molecules is important, as these are potential defense signals or signal intermediates.

SUMMARY

Azelaic acid and its derivatives or analogs prime plants to activate their resistance response against a pathogen attack. Azelaic acid and its derivatives induce a plant defense response prior to pathogen attack in the absence of activating expression of most defense-related genes.

A method of increasing resistance to a pathogen in a plant includes:
  (a) obtaining a composition including an effective amount of azelaic acid or an analog or a derivative thereof; and
  (b) contacting a plant component with the composition to increase resistance to the pathogen in the plant.

A suitable plant component is selected from a group that includes leaves, roots, stems, fruits, flowers, and seeds.

A suitable azelaic acid derivative is generally water-soluble. Examples of azelaic acid derivatives include sodium azelate, potassium azelate, and azelaic acid esters.

A method of priming a plant to induce its defense mechanism against a pathogen includes:
  (a) obtaining a composition including azelaic acid or an analog or a derivative thereof; and
  (b) contacting the plant with the composition to prime the plant to induce its defense mechanism in response to a pathogen attack.

A method of protecting a plant against a pathogen infection includes:
  (a) providing a composition including azelaic acid or an analog or a derivative thereof; and
  (b) exposing the plant to the composition to protect the plant against the pathogen infection.

Some examples of plant pathogens include bacterial, fungal, oomycete, and viral plant pathogens. Suitable plants for treatment as described herein include monocots and dicots. For example, a monocot plant is a crop plant. A suitable plant is also an ornamental plant.

Azelaic acid concentration in a composition may include a range of about 0.01 mM to 10 mM and any intervening concentrations such as 0.1 mM, 0.5 mM, 1 mM, 2 mM, and 5 mM. If azelaic acid is mixed with one or more of other defense inducing components, the concentration of azelaic acid may be lower. Azelaic acid or its derivative, including analogs, are sprayed over a plant foliage. The composition may also be taken up through the plant roots. The composition is generally administered in the presence of light.

The compositions disclosed herein may also be administered as a combination with a plant nutrient. The composition may be administered prior to a pathogen attack or during a pathogen attack.

The compositions may also include a component to induce defense mechanisms that depend on ethylene or jasmonic acid.

A method of inducing disease resistance in a plant includes:
  (a) pre-treating the plant with an effective concentration of a composition consisting essentially of azelaic acid and any other component that does not materially affect the functioning of azelaic acid;
  (b) inducing disease resistance in plants by priming the plant's defense response against a pathogen.

A method of inducing systemic acquired resistance response in a plant includes:
  (a) applying a composition including azelaic acid or an analog or a derivative thereof to one or more parts of the plant; and
  (b) inducing a systemic resistance response in the entire plant against a pathogen.

A method of priming a plant against a pathogen infection includes:

(a) contacting the plant with a composition including a component of a plant exudate, wherein the composition does not significantly induce pathogenesis-related protein 1 (PR-1); and (b) priming the plant against the pathogen infection.

A method of inducing pathogen resistance in a plant includes:

(a) contacting the plant with a composition including azelaic acid or a derivative thereof;

(b) contacting the plant with an agent that activates one or more plant defense responses; and (c) inducing pathogen resistance in the plant.

A suitable agent that can be used along with azelaic acid or its derivative includes for example, salicylic acid agonists, reactive oxygen species, benzothiazole, jasmonic acid, and ethylene.

A plant defense-inducing composition includes an effective amount of azelaic acid or a derivative thereof and a plant nutrient.

A plant growth-promoting composition includes an effective amount of azelaic acid or a derivative thereof and a plant nutrient.

DETAILED DESCRIPTION

Figure 1:
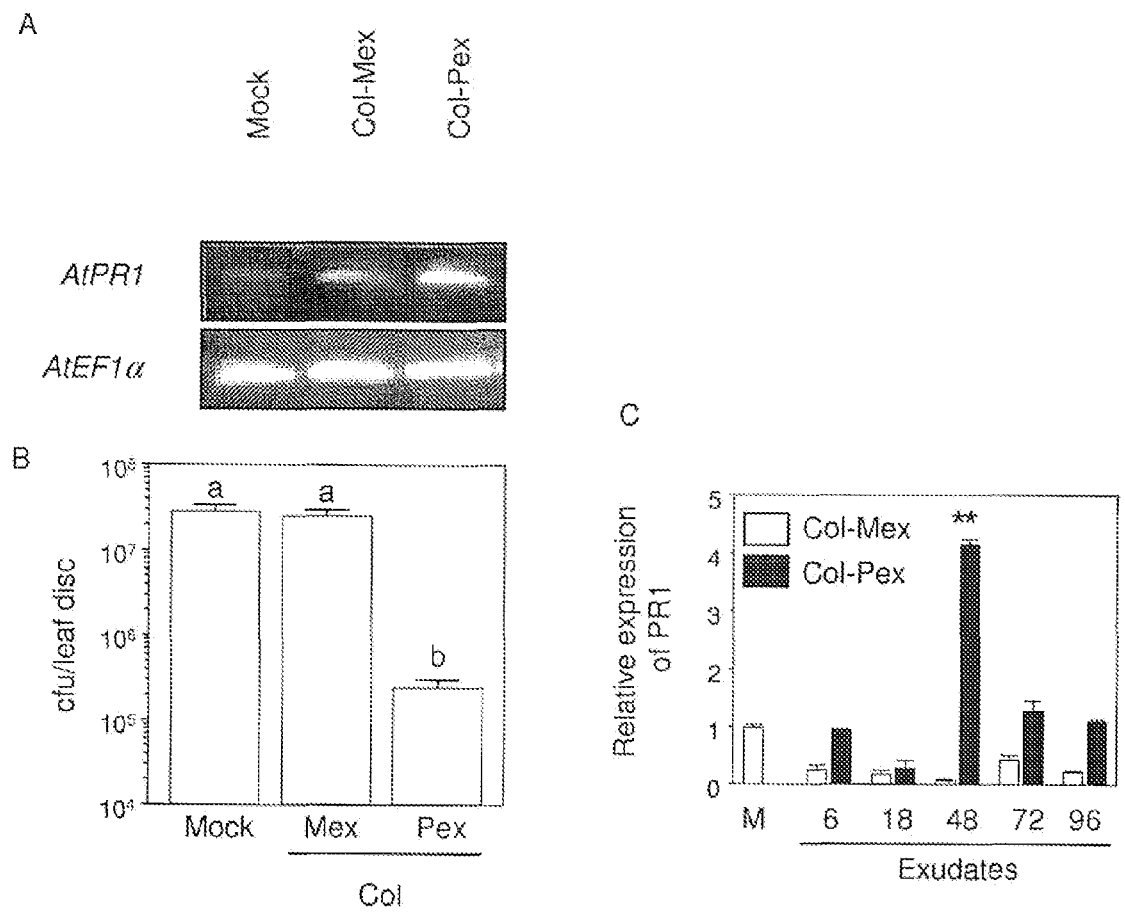
FIG. 1 demonstrates that petiole exudates from pathogen-infected plants have signaling compounds that induce disease resistance and defense markers in *Arabidopsis* Col plants. (A) PR1 expression in leaves of wild-type Col at 2 days after treatments with 0.25 mM EDTA and petiole exudates from mock-treated Col (Col-Mex) and from *Pseudomonas syringae* pv. *maculicola* carrying avrRpt2-inoculated Col (Col-Pex). AtEF1-α was used as an internal control for the quantity of mRNA. (B) Reduced bacterial growth in Col leaves pre-treated by syringe-inoculation with pathogen-induced petiole exudates (Col-Pex). Different letters indicate statistically significant differences (P<0.001, t-test, n=6). (C) Relative gene expression in Col leaves at 2 days after infiltrating different exudates that were collected at various times after pathogen inoculation. The number of asterisks indicates samples that were different from one another at given level of statistical significance (**p<0.01). 0.25 mM EDTA was applied as a control (M).

Disclosed herein are methods and compositions that induce disease resistance in plants by activating endogenous defense mechanisms. Azelaic acid, a plant exudate component, is shown to prime plants against pathogen attack. Azelaic acid by itself enhances protection against pathogen attack in plants by activating a plant's underlying signaling mechanism in the absence of a substantial induction of 'defense genes' (e.g., pathogenesis related (PR) genes). However, upon pathogen attack the azelaic acid-treated plants display enhanced protection against pathogen infection compared to untreated plants. This protection is accompanied by a stronger activation of defense responses indicating that the azelaic acid treatment primes the plant's resistance response against pathogen attack. Azelaic acid treatment does not impose a significant metabolic burden on the plants in the absence of a pathogen attack. Structural and functional analogs and derivatives of azelaic acid are also suitable in activating a plant's resistance response against pathogens.

Compositions that include an effective amount of azelaic acid are applied to the plants by appropriate methods of application known to those of ordinary skill in the art. For example, stable formulations of azelaic acid or its derivatives are included along with plant nutrient mix as part of a root feeding approach. Leaf wetting agents such as, for example, a surfactant may also be used when aerial spraying is used to contact the plants with azelaic acid or its derivatives. The compositions can be applied by, for example, spraying, atomizing, dusting, scattering, coating or pouring, introducing into or on the soil, introducing into irrigation water, by seed treatment, or dusting at a time when the plant pathogen has begun to appear or before the appearance of pathogens as a protective measure. Any means that bring the azelaic acid-based compositions in contact with the plants can be used in the practice of the embodiments. The compositions can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, or also encapsulations in, for example, polymer substances.

Azelaic acid or its derivative-containing compositions disclosed herein may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth.

Agronomically acceptable carriers are known and include, for example, solid carriers such as fine powders or granules of kaolin clay, attapulgite clay, bentonite, acid clay, pyrophillite, talc, diatomaceous earth, calcite, corn starch powder, walnut shell powder, urea, ammonium sulfate, synthetic hydrated silicon dioxide and the like. Acceptable liquid carriers include, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cottonseed oil, corn oil and the like, dimethyl sulfoxide, acetonitrile, water and the like.

Suitable wetting agents include for example alkyl benzene and alkyl naphthalene sulfonates, alkyl and alkyl aryl sulfonates, alkyl amine oxides, alkyl and alkyl aryl phosphate esters, organosilicones, fluoro-organic wetting agents, alcohol ethoxylates, alkoxylated amines, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, block copolymers, polyoxyalkylene derivatives of alkylphenols (particularly isooctylphenol and nonylphenol) and polyoxyalkylene derivatives of the mono-higher fatty acid esters of hexitol anhydrides (e.g., sorbitan). Dispersants include methyl, cellulose, polyvinyl alcohol, sodium lignin sulfonates, polymeric alkyl naphthalene sulfonates, sodium naphthalene sulfonate, polymethylene bisnaphthalene sulfonate, and neutralized polyoxyethylated derivatives or ring-substituted alkyl phenol phosphates. Stabilizers may also be used to produce stable emulsions, such as magnesium aluminum silicate and xanthan gum.

Suitable concentrations of azelaic acid or its derivatives range from about 0.1 mM to about 1000 mM, including any of the intervening concentrations such as 1 mM, 10 mM, 20 mM, 50 mM, 100 mM and 500 mM. Depending on the nature of the plants, the age of the plants, the mode of administration, and the environmental conditions, either lower or higher concentrations of azelaic acid may also be applied. In addition, depending upon the stability, toxicity, and effectiveness of azelaic acid analogs or derivatives, suitable concentration may range from about 0.01 mM to about 10 mM. Optimal concentrations of azelaic acid and its derivatives or analogs are determined by using one or more of the methods disclosed herein by measuring, for example, pathogen growth after infection or gene expression, or by determining any suitable resistance response marker. Compositions that consist essentially of azelaic acid or its derivatives may be in the form of a stock suspension or in a dry state.

Some of the desirable considerations for azelaic acid analogs and derivatives include extended in vivo and ex vivo stability, increased effectiveness, reduced plant toxicity, capability of being absorbed through the leaves and/or roots, and reduced side effects, if any, upon human consumption of any left-over derivatives or analogs through plant products. The analogs and derivatives include structural analogs of azelaic acid as well as formulations that extend the stability or effectiveness or both of azelaic acid.

Azelaic acid or its derivatives may also be used in combination with other compositions that enhance the plant resistance response against pathogens. For example, a suitable amount of azelaic acid or its derivatives can be mixed with a suitable amount of a compound, such as, for example salicylic acid (SA) or SA agonists such as 2,6-dichloroisonicotinic acid (INA), 3-hydroxypicolinic acid and benzo(1,2,3)thiadiazole-7-carbothioic acid S-methyl ester (BTH or benzothiadiazole) that activate the salicylic acid response in plants. Similarly, a suitable amount of azelaic acid or its derivatives can be mixed with a suitable amount of a compound that activates jasmonic acid and ethylene signaling pathways. Additionally, a suitable amount of azelaic acid or its derivatives can be mixed with a suitable amount of a reactive oxygen species for example, peracetic acid or a peroxide compound, or a compound that generates reactive oxygen intermediates, such as a redox-cycling agent. Similarly, a suitable amount of azelaic acid or its derivatives can be mixed with a suitable amount of an elicitor, such as Harpin, which mimic a pathogen attack on a plant. SA, SA agonists such as BTH, reactive oxygen species, elicitors or any other defense inducing compound can be either applied along with azelaic acid or after the application of azelaic acid. These additional defense inducing compounds may also be applied prior to azelaic acid application. Concentrations for these additional defense-inducing compounds may vary from about 0.1 µM to about 100 µM or 1 mM. If these additional compounds are applied after the application of azelaic acid, a period of about 4-24 hours is given between the serial applications. Booster applications of either azelaic acid or these additional compounds may be practiced as well.

The term "azelaic acid derivatives" include any chemical(s) that are derived from azelaic acid, for example a particular salt of azelaic acid. Azelaic acid derivatives also include structural analogs. Azelaic acid derivatives include esters of azelaic acid that include for example, dimethyl-azelate, diethyl-azelate, dipropyl-azelate, dihexyl-azelate, di-(t-butyl)-azelate and the like. Additional derivatives include for example, azeloyl glycine, mono- or di-sodium salts, mono- or di-potassium salts of azelaic acid. Generally, azelaic acid derivatives increase either water-solubility if needed and/or stability.

Compositions that include azelaic acid or its derivatives may contain about 95% pure azelaic acid or 90% pure or 85% pure or 85% pure or more than about 75% pure azelaic acid. Crude or partially purified plant exudates that contain an effective amount of azelaic acid or its derivatives are also suitable to be used as a composition.

The term "consisting essentially of" refers to compositions that contain azelaic acid or its derivatives or analogs as an active ingredient and may optionally contain any other component that does not materially affect the functional attributes of azelaic acid e.g., in inducing resistance response in plants. For example, a composition consisting essentially of azelaic acid may include a wetting agent or a carrier.

The terms "exposing" and "contacting" refer to one or more methods of treating plants with azelaic acid or its derivatives by any suitable method, such as, for example spraying or infiltrating or root feeding.

The term "priming" refers to the process by which a plant is prepared to mount an effective resistance response against pathogens.

The term "defense-related genes" refers to one or more genes that are induced at least more than 2 or 3 or 5-fold within a few hours after pathogen attack. These defense-related genes include the pathogenesis-related (PR) genes. For example, PR-1 is a suitable defense-related gene. Defense-related genes may also be considered defense-related markers.

The term "systemic acquired resistance" (SAR) refers to a whole-plant resistance response upon pathogen attack (or any other resistance inducing treatment) on one part of the plant.

The term "antimicrobial" or "antimicrobial activity" refers to antibacterial, antiviral, antinematodal, and antifungal activity against plant pathogens. Accordingly, the azelaic acid and its derivatives may enhance resistance to insects and nematodes that infest plants.

The terms "plant pathogen" or "plant pest" refer to any organism that can infect and cause harm to a plant. A plant can be harmed by an inhibition or slowing of the growth of a plant, by damage to the tissues of a plant, by a weakening of the defense mechanism of a plant, by a reduction in the resistance of a plant to abiotic stresses, by a premature death of the plant, and the like. Plant pathogens and plant pests include, but are not limited to nematodes, and organisms such as fungi, oomycetes, viruses, and bacteria.

The terms "disease resistance" or "pathogen resistance" are intended to mean that the organisms avoid the disease symptoms that are the outcome of organism-pathogen interactions. That is, pathogens are prevented from causing diseases and the associated disease symptoms, or alternatively, the disease symptoms caused by the pathogen are minimized or lessened.

The term "plant component" refers to any plant material that is likely to be attacked by a pathogen. Suitable plant component includes for example, leaves, stems, roots, flowers, fruits, seeds, seedlings, callus, tubers, and plant cell culture.

Azelaic acid-based compositions may reduce the disease symptoms resulting from pathogen challenge by at least about 5% to about 50%, at least about 10% to about 60%, at least about 30% to about 70%, at least about 40% to about 80%, or at least about 50% to about 90% or greater.

Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctonus*), wheat (*Triticum aestivum*), soybean (*Glycine max*), tobacco (*Nicotiana tabacum*), potato (*Solanum tuberosum*), citrus trees (*Citrus* spp.), cocoa (*Theobroma cacao*), tea (*Camellia sinensis*), oats, barley, vegetables, ornamentals, and conifers.

Vegetables include for example, tomatoes (*Lycopersicon esculentum*), lettuce (e.g., *Lactuca sativa*), green beans (*Phaseolus vulgaris*), lima beans (*Phaseolus limensis*), peas (*Lathyrus* spp., *Pisum* spp.). Ornamentals include for example, azalea (*Rhododendron* spp.), hydrangea (*Hydrangea macrophylla*), hibiscus (*Hibiscus rosasanensis*), roses (*Rosa* spp.), tulips (*Tulipa* spp.), daffodils (*Narcissus* spp.), and chrysanthemum.

Pathogens of the embodiments include, but are not limited to, viruses or viroids, bacteria, nematodes, fungi, and the like. Viruses include any plant virus, for example, tobacco or cucumber mosaic virus, ringspot virus, necrosis virus, maize dwarf mosaic virus, and the like. Specific fungal, oomycete and viral pathogens for the major crops include, but are not limited to the following: *Phytophthora, Fusarium* spp., *Alternaria, Pythium* spp., Soybean mosaic virus, Tobacco Ring spot virus, Tobacco Streak virus, Tomato spotted wilt virus, *Sclerotinia, Peronospora, Cladosporium, Erysiphe, Aspergillus, Puccinia* spp., and *Trichoderma*. Specific bacterial plant pathogens include any bacterial species that infect plants and include, but are not limited to *Xanthomonas* (e.g., *Xanthomonas axonopodis* pv. *aurantifolii, Xanthomonas campestris* pv. *campestris, Xanthomonas campestris* pv. *vesicatoria*), *Pseudomonas* (*Pseudomonas syringae* pv. *tomato, Pseudomonas syringae* pv. *phaseolicola, Pseudomonas syringae* pv. *syringae*), *Erwinia* (e.g., *Erwinia carotovora* subsp. *atroseptica*), *Ralstonia* (e.g., *Ralstonia solanacearum*), *Clavibacter michiganensis*, and *Xylella fastidiosa*.

EXAMPLES

The following examples are for illustrative purposes only and are not intended to limit the scope of the disclosure.

Example 1

Petiole Exudates Induce Defense Responses Against *Pseudomonas syringae* Infection To induce the production of possible defense-inducing signal molecules, *Arabidopsis* leaves were infiltrated with an avirulent derivative of *Pseudomonas syringae* pv. *maculicola* ES4326 carrying avrRpt2 (strain PmaDG6) that induces systemic acquired resistance (SAR). Infiltration with 10 mM $MgSO_4$ served as a mock inoculation control. After 12-15 hours, leaves were excised and placed in 1 mM EDTA for the collection of exported material, presumed to be phloem components, from the petioles. The EDTA blocks the production of callose at the wound site and prevents the plugging of the cut end, thereby allowing the collection of potential defense-inducing signal molecules. Quarter-strength bacteria-free petiole exudates were infiltrated into leaves to test their ability to activate defense responses. FIG. 1A shows the expression levels of PR1, a salicylic acid (SA) signaling marker, in leaves at 2 days after treatment with 0.25 mM EDTA, mock-induced exudate (Col-Mex) or pathogen-induced exudate (Col-Pex). The Col-Pex triggered a high level of PR1 expression, relative to that found after treatment with Col-Mex. These data indicate that there is one or more biologically active signal molecules in the Col-Pex that is able to induce PR1 expression.

To test whether the Col-Pex could also confer resistance to pathogen infection, a virulent derivative of *P. syringae* pv. *maculicola* ES4326 carrying empty vector (strain PmaDG3) was inoculated onto leaves of 25-day-old plants 2 days after pretreatment with exudates. Bacterial growth after three days was significantly reduced in leaves pretreated with Col-Pex, compared with those of mock-treated and Col-Mex-treated plants (FIG. 1B). These data show a biological activity of petiole exudates from leaves inoculated with avirulent bacteria.

Signal molecule(s) found in active exudates might be induced at a distinct time after infection with SAR-inducing bacteria. Therefore, petiole exudates were collected at various times after infection with avirulent PmaDG6 and quarter-strength exudates were infiltrated into leaves which were analyzed for PR1 expression 2 days after treatment (FIG. 1C). Expression levels were normalized to those found in 0.25 mM EDTA-treated plants. Petiole exudates collected at 48 and 72 hrs after pathogen inoculation induced PR1 expression. The level of PR1 expression was significantly higher in leaves infiltrated with Col-Pex collected 48 hrs after pathogen inoculation.

Figure 2:
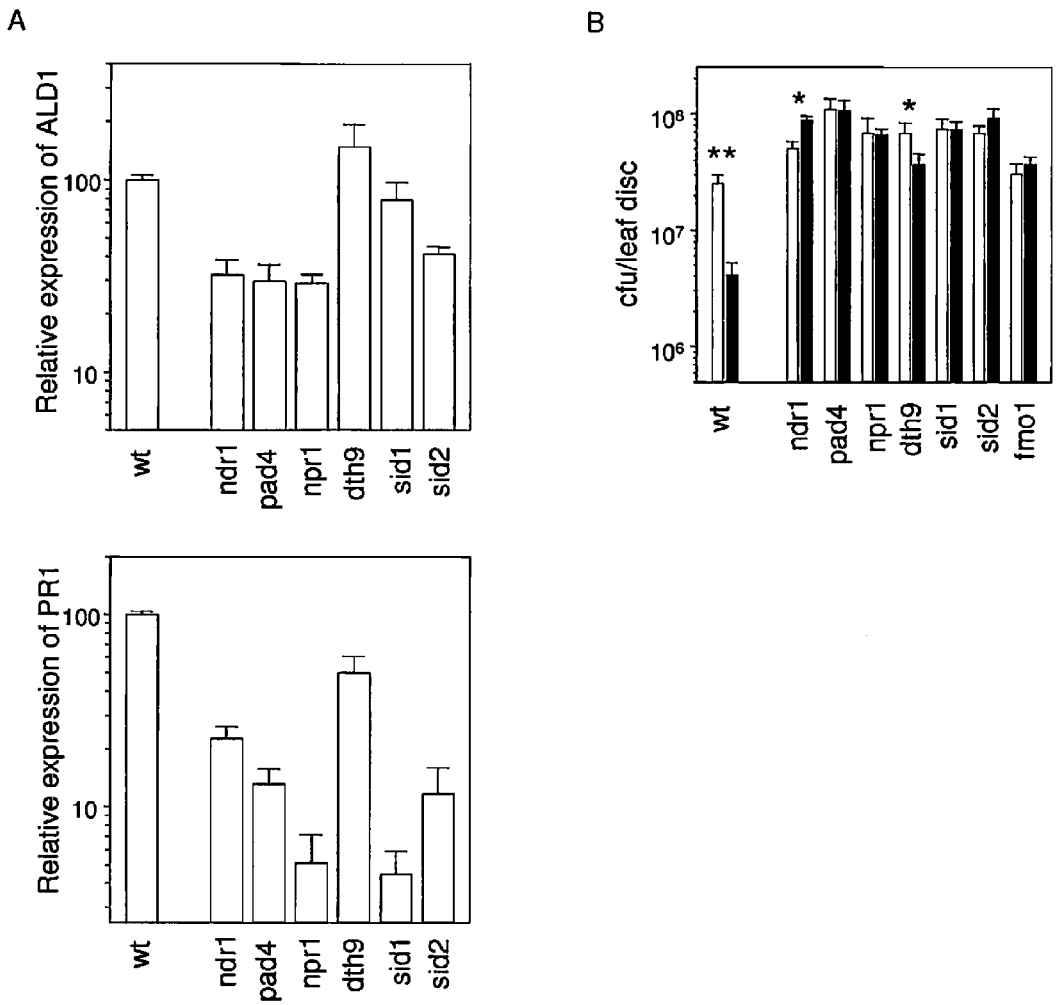
FIG. 2 illustrates that some defense mutants show attenuated defense-related gene induction and/or pathogen resistance induced by Col-Pex exudates. (A) Relative defense-related gene expression in leaves of wild-type (WT) (Col) and mutant plants at 2 days after treatment of active exudates. (B) *Pseudomonas syringae* pv *maculicola* strain PmaDG3 growth in leaves of wild-type Col and mutant plants treated with Col-Mex (white bars) and Col-Pex (line bars). PmaDG3 (OD600=0.0001) was infiltrated into leaves at 2 days after pre-treatment of exudates. The growth of bacteria was measured on day 3 after inoculation. The number of asterisks indicates samples that were different from one another at a given level of statistical significance (*p<0.05, **p<0.005)

It was also tested whether the active exudates could induce ALD1 and PR1 expression in a series of SAR-defective and SA-deficient mutants. The active Col-Pex exudate was infiltrated into leaves of wild-type and mutant plants 2 days prior to collecting tissues for isolation of total RNA. FIG. 2A shows relative PR1 expression levels in different mutants normalized to expression in wild-type leaves. Col-Pex only weakly induced PR1 expression in leaves of ndr1, pad4, npr1, sid1 and sid2. These data indicate that these cellular components essential for SAR were also required for the response to a signal molecule(s) in petiole exudates. Moreover, plant resistance induced by Col-Pex was completely abolished in the SAR-defective and SA-deficient mutants tested (FIG. 2B). Col-Pex was still active in dth9 mutant plants (p<0.05, student t-test), which are known to be compromised for the maintenance of SAR, and are unable to induce resistance in response to SA treatment.

Example 2

A High Level of Azelaic Acid Accumulates in Active Petiole Exudates

Metabolites in active exudates were compared with those in mock-induced exudates to discover the molecule(s) responsible for inducing plant defenses. The levels of about 160 metabolites in exudates were analyzed using gas chromatography (using a 95% dimethyl/5% diphenylpolysiloxane column) coupled with mass spectrometry (GC-MS). High levels of azelaic acid ($C_9H_{16}O_4$) were detected in active Col-Pex preparations, compared with those in Col-Mex (Table 1). The differences of the response ratios from each experiment largely resulted from variation in basal levels of azelaic acid in plants grown at different times.

Figure 7:
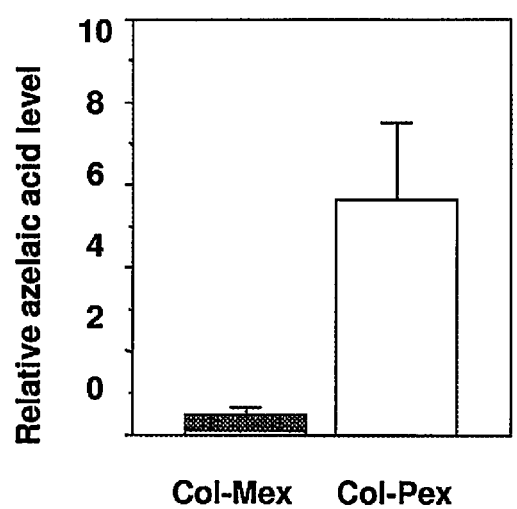
FIG. 7 demonstrates that exudates from pathogen-infected plants contain significantly more azelaic acid than exudates from mock treated plants. Exudate samples from leaves treated with PmaDG6 (Col-Pex) or 10 mM MgSO4 (Col-Mex) for 72 hrs were analyzed using GC-MS. The active exudates contained an average of 6.2 fold higher levels of azelaic acid compared to inactive exudates (5.1 uM in mock-induced exudates, 31.6 uM in pathogen-induced exudates, p=0.042, t-test).

As shown in FIG. 7, active exudates contained an average of 6.2 fold higher levels of azelaic acid than inactive exudates.

TABLE 1

Relative level of azelaic acid in petiole exudates either from mock-treated or pathogen-inoculated wild-type Col *Arabidopsis*

| Compound | Mol. formula[1] | R.T. (min)[2] | TIC (%)[3] | PC[4] |
|---|---|---|---|---|
| Azelaic acid | C9H16O4 | 17.14 | 317 | 95% dimethyl/5% diphenyl polysiloxane |

| Trial | Col-Mex[5] Avg. | Col-Pex[6] Avg. | Response ratio Pex/Mex |
|---|---|---|---|
| 1 | 0.09 | 3.42 | 37.26 |
| 2 | 0.5 | 12.03 | 24.13 |
| 3 | 1.15 | 2.07 | 1.8 |
| 4 | 2.31 | 3.37 | 1.46 |
| 5 | Not detected | 10 | >10 |

[1]Molecular formula; [2]Retention time; [3]Total Ion Current; [4]Polymer of Coating Material; [5]Mex, Mock-treated exudate; [6]Pex, PmaES4326/avrRpt2-induced exudate (OD600 = 0.01)

Example 3

Figure 3:
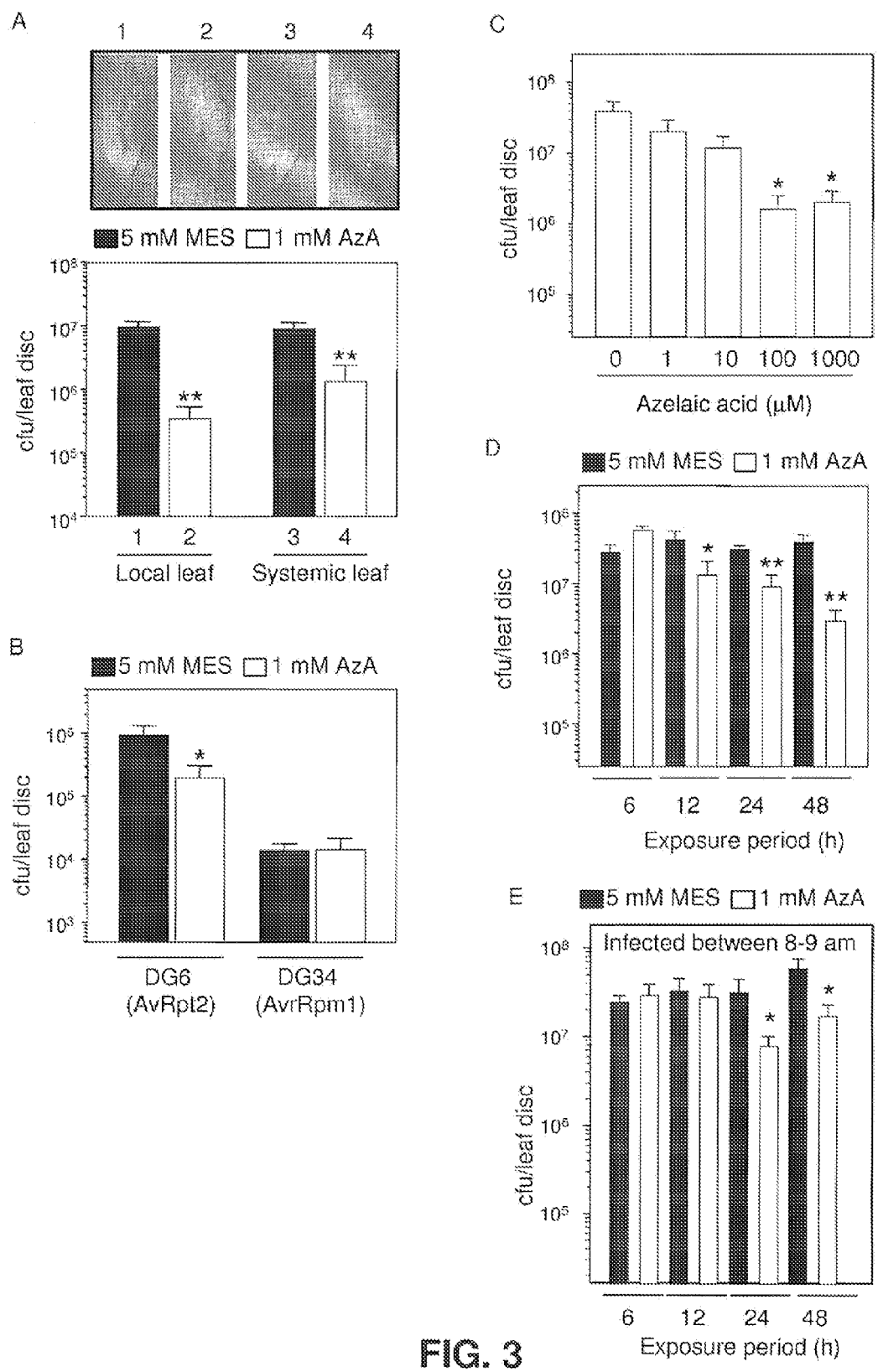
FIG. 3 demonstrates that the petiole exudate component azelaic acid induces plant resistance against PmaDG3 infection. (A) Local and systemic resistance response by azelaic acid treatment against virulent PmaDG3 infections. Local or systemic leaves of 21~23-day-old plants were treated with 5 mM MES (pH 5.6) (black bars) or 1 mM azelaic acid in 5 mM MES (pH 5.6, white bars) 2 days prior to challenge with the virulent PmaDG3 strain (OD600=0.0001). MES and azelaic acid were introduced into leaves by syringe-infiltration. Azelaic acid induced a significant reduction in the disease symptoms of local and systemic leaves and a reduction in pathogen growth. (B) Growth of avirulent strains PmaDG6 (PmaDG3 carrying avrRpt2) and PmaDG34 (PmaDG3 carrying avrRpm1) in leaves of Col pretreated with 5 mM MES (black bars) or 1 mM azelaic acid in 5 mM MES (pH 5.6, white bars). (C) Twenty three-day-old plants were pretreated with 1, 10, 100, and 1000 μM azelaic acid in 5 mM MES or 5 mM MES for 2 days and then subjected to infection with virulent PmaDG3 at OD600=0.0001. The 100 and 1000 μM azelaic acid treatments resulted in significant reduction of the growth of bacteria under the conditions tested. (D) Plants were treated with 5 mM MES or 1 mM azelaic acid for the indicated times prior to inoculation with virulent PmaDG3. Inoculations with PmaDG3 were performed between noon and 1 pm. Azelaic acid (Aza) in 5 mM MES was applied to plants using a hand-sprayer. The growth of bacteria was measured on day 3 after inoculation. The number of asterisks indicates samples that were significantly different from one another at given level (*p<0.05, **p<0.01). Significant protection occurred when inoculations were performed 48 h after spraying plants. (E) Plants were treated and infected as in (D), except that infections were performed between 8 and 9 μm. (*p<0.04). These experiments were repeated two to four times to confirm reproducibility.

Azelaic Acid Confers Resistance Responses Against *Pseudomonas syringae* Infection Biological activity of azelaic acid in inducing disease resistance. 1 mM azelaic acid was infiltrated into leaves 3 and 4 of 3-week old plants. Two days later, plants were inoculated with virulent PmaDG3 onto leaves 3 and 4 or in the upper leaves, which were not pre-treated with azelaic acid (systemic leaves). Azelaic acid (1 mM) dissolved in 5 mM MES (pH 5.6) was not toxic to plant cell. The growth of PmaDG3 was significantly reduced in both local and systemic leaves of azelaic acid-treated plants, compared with those of mock-treated plants (FIG. 3A). Unlike mock-treated plants, azelaic acid-treated plants showed very little disease symptom development. Mock-treated and azelaic acid-treated plants were also infiltrated with avirulent derivatives of *P. syringae* pv. *maculicola* carrying avrRpt2 (PmaDG6) or avrRpm1 (PmaDG34). Azelaic acid caused a reduction in the growth of PmaDG6 (carrying avrRpt2), but not PmaDG34 (carrying avrRpm1; FIG. 3B).

PmaDG3 growth was measured after spray treatment of plants with various concentrations of azelaic acid. FIG. 3C shows that plants pretreated with 100 and 1000 µM of azelaic acid were resistant to PmaDG3. This induced resistance resulted in a 10-fold suppression of bacteria growth. In contrast, there was no difference in bacterial growth after treatments with 5 mM MES and 1 or 10 µM azelaic acid at the conditions tested. It was also tested whether azelaic acid required a certain induction period for the induced resistance response. Plants grown in the light and pretreated with azelaic acid using a hand sprayer 6 hours prior to infection were still susceptible to virulent *P. syringae* (FIG. 3D), while pretreatment 12 hours prior to pathogen challenge conferred a low level of resistance (FIG. 3D). However, when plants were grown in the dark for 12 hours after treatment, azelaic acid was ineffective at conferring disease resistance (FIG. 3E). The induced-resistance was more stable and stronger with longer times of exposure to azelaic acid. Thus, azelaic acid induces a light-dependent disease resistance response against infection with *P. syringae* that is also concentration- and time-dependent.

Example 4

Figure 4:
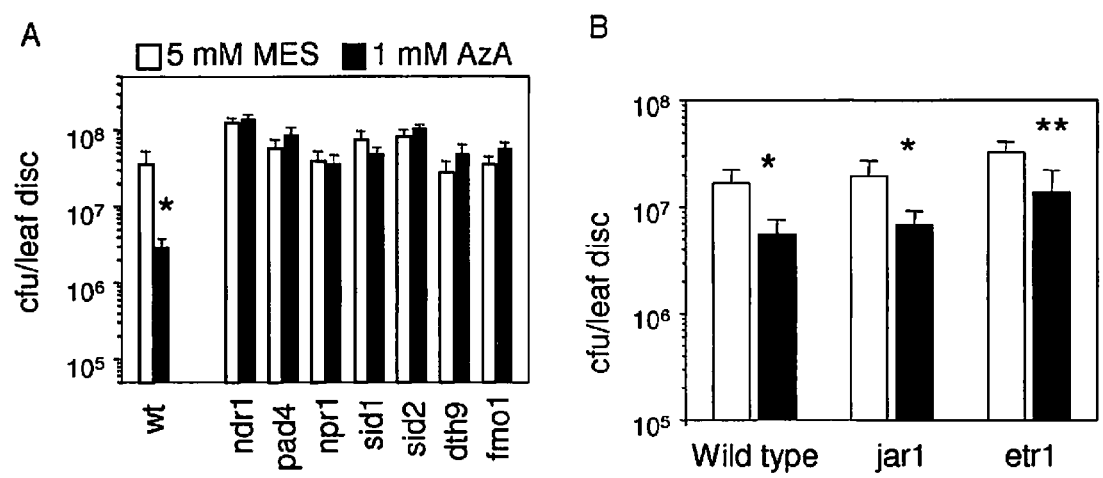
FIG. 4 shows *Pseudomonas syringae* (strain PmaDG3) growth in leaves of plants defective for systemic acquired resistance (SAR) and salicylic acid (SA)-deficient mutants. 1 mM azelaic acid in 5 mM MES was applied to wild-type Col, SAR-defective, and SA-deficient mutants (A) and jasmonic acid/ethylene-insensitive mutants (B) 2 days prior to challenge-inoculation of virulent PmaDG3 (OD600=0.0001). Azelaic acid did not induce plant resistance in the SAR-defective and SA-deficient mutants tested herein. This suggests that these cellular components were required for azelaic acid-induced resistance response in *Arabidopsis*. By contrast, jar1 and etr1 mutation did not affect azelaic-induced resistance in *Arabidopsis*. The experiments were repeated a minimum of three times. The number of asterisks indicates samples that were different from one another at given levels of statistical significance (*p<0.05, **p<0.01).

Azelaic Acid-Induced Resistance is Attenuated in SAR-Defective, SA-Insensitive and SA-Deficient Mutants, but not JA/Ethylene-Insensitive Mutants To further characterize how plants regulate azelaic acid-induced resistance, 1 mM azelaic acid was sprayed onto wild type and several mutant plants 2 days before infection with virulent PmaDG3 and bacterial growth was measured. Unlike wild-type plants, the SA pathway mutants tested were susceptible to virulent PmaDG3 infection regardless of treatment with azelaic acid (FIG. 4A). These data demonstrate that multiple defense components (NDR1, PAD4, NPR1, SID1, SID2, and FMO1) known to be important to regulate, synthesize and respond to SA may play a role for azelaic acid-induced plant resistance in the plants tested in this example. Pathogen resistance was also dependent on DTH9, which is important for SA-induced disease resistance and SAR maintenance in *Arabidopsis*. The growth of bacteria was also monitored in leaves of JA- and ethylene-insensitive mutants, jar1 and etr1, following treatment with 1 mM azelaic acid. FIG. 4B shows that treatment of azelaic acid was effective in restricting bacterial growth in jar1 and etr1 mutants suggesting that jasmonic acid and ethylene-dependent signaling are dispensable for azelaic acid-induced resistance in *Arabidopsis*.

Example 5

Figure 5:
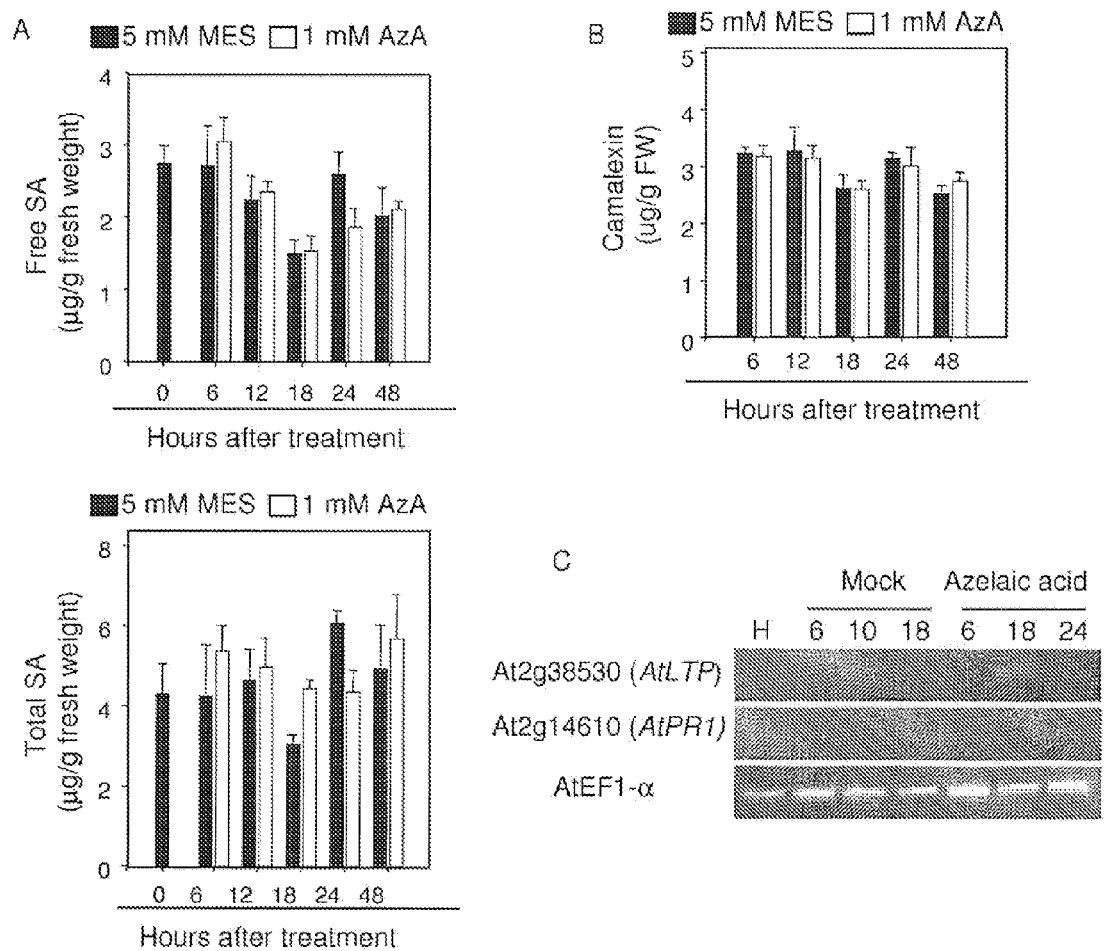
FIG. 5 shows that azelaic acid does not affect endogenous salicylic acid and camalexin levels but does induce expression of a lipid transfer protein (LTP) gene in wild-type Col *Arabidopsis*. (A) Time course of free and total salicylic acid levels in leaves of Col after spray treatments with 5 mM MES (black bars) and 1 mM azelaic acid in 5 mM MES (white bars). (B) Camalexin levels in leaves of Col after azelaic acid treatment by spraying. Each experiment in (A) and (B) was performed with three different samples and the experiments were repeated three times. (C) Expression of an LTP gene (At2g38530) was elevated after azelaic acid treatment performed as in (A), however expression of PR1 and many other defense-related genes was unaffected. RT-PCR (23 cycles) was used to assess gene expression, with EF1a serving as a loading control.

Exogenous Treatment of Azelaic Acid Does Not Increase Salicylic Acid or Camalexin Levels Since resistance to *P. syringae* requires activation of SA-dependent defenses accompanied by elevated endogenous SA levels, it was investigated whether azelaic acid directly induces SA accumulation. After spray treatment of plants with 1 mM azelaic acid, there was no significant difference in free and total SA level between mock-treated and azelaic acid-treated plants (FIG. 5A). Additionally, the levels of the phytoalexin Camalexin, a defense metabolite, were similar in azelaic acid-treated and mock-treated plants (FIG. 5B). These data indicate that azelaic acid does not directly affect the levels of either SA or camalexin. To investigate whether azelaic acid might affect additional defense markers, expression of defense-related genes was monitored using a mini array. Surprisingly, most defense-related genes that were tested showed no difference in expression between mock-treated and azelaic acid-treated plants. One gene encoding a potential lipid transfer (LTP) protein, At2g38530, was significantly induced (3-fold) by azelaic acid. RT-PCR confirmed that At2g38530 was induced by azelaic acid. However, PR1, a SA signaling marker, was not induced by azelaic acid. Thus, azelaic acid appears not to induce large changes in known signaling pathways activated by *P. syrinagae*, but does induce at least one defense-related gene.

Example 6

Azelaic Acid Primes Defense Responses

Figure 6:
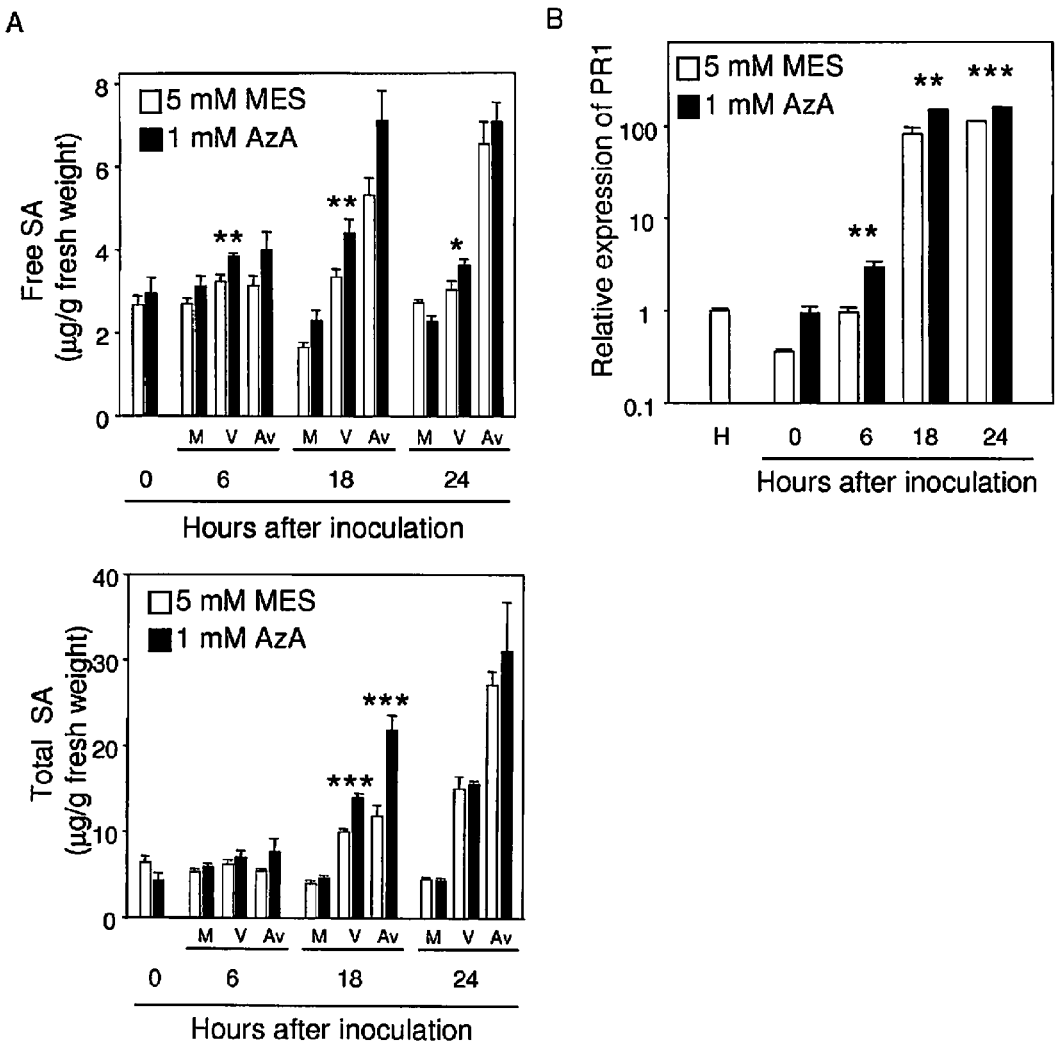
FIG. 6 demonstrates that azelaic acid primes SA-dependent defense signaling. (A) Endogenous free and total SA levels in azelaic acid-treated plants were significantly higher than those in mock-treated plants during *Pseudomonas syringae* infections. Five mM MES or 1 mM azelaic acid in 5 mM MES were applied to leaves of wild-type Col *Arabidopsis* 2 days prior to inoculation of 10 mM MgSO$_4$ (M), virulent PmaDG3 (V) and avirulent PmaDG6 expressing AvrRpt2 (Av). Leaves were collected at different times after inoculation and endogenous free and total SA level was measured. (B) Relative PR1 expression in leaves of mock-treated plants and azelaic acid-treated plants after virulent PmaDG3 infection. The expression of PR1 is plotted on a log scale. The number of asterisks indicates samples that were different from one another at given levels of statistical significance (*p<0.075, p<0.05, *p<0.01).

Since SA signaling mutants were compromised in responding to azelaic acid, it was investigated whether azelaic acid might prime SA synthesis or SA-dependent defense responses in plants. To test this, plants were sprayed with 1 mM azelaic acid (or 5 mM MES) and after two days infected with virulent PmaDG3 and avirulent PmaDG6 (carrying avrRpt2) (OD600=0.01). FIG. 6A shows that the levels of free SA in azelaic acid-treated plants were significantly higher than those in mock-treated plants at 6 and 18 hrs after virulent PmaDG3 infection ($p<0.05$, student t-test). A similar trend was seen after infection with PmaDG6 (carrying avrRpt2), but the results were not statistically significant. Additionally, pretreatment of azelaic acid resulted in a higher level of total SA accumulation at 18 hrs after inoculation with both PmaDG3 and PmaDG6, compared with those of mock-treated plants ($p<0.01$, student t-test). The priming effect by azelaic acid was also investigated by analyzing PR1 expression, a molecular marker for SA signaling (FIG. 6B). Mock- and azelaic acid-treated plants were infected with virulent PmaDG3 (OD600=0.01) 2 days after spray treatments. PR1 expression was increased in both azelaic acid treated and untreated plants after infection with the virulent strain. However, the expression was higher in leaves pretreated with azelaic acid after pathogen infection, compared with expression in mock-treated plants following pathogen infection (note the log scale in FIG. 6B). These data indicate that the mode of action of azelaic acid is to prime plants to induce defenses more strongly and more quickly than untreated plants.

The invention claimed is:

1. A method of priming a plant to induce resistance response against a pathogen, comprising:
   contacting a component of the plant with an exogenous composition comprising an ionic form of purified azelaic acid, wherein the composition is essentially non-toxic to the plant.

2. The method of claim 1, wherein the plant component is plant foliage.

3. The method of claim 1, wherein the resistance response is systemic acquired resistance.

4. The method of claim 1, wherein the composition is administered prior to a pathogen attack.

5. The method of claim 1, wherein the plant is a crop plant.

6. The method of claim 1, wherein the composition is a solution.

7. The method of claim 1, wherein the pathogen is selected from bacterial, fungal, oomycete, and viral plant pathogens.

8. The method of claim 1, wherein the plant is a monocot.

9. The method of claim 1, wherein the plant is an ornamental plant.

10. The method of claim 1, wherein the azelaic acid is in a concentration range of about 0.01 mM to 10 mM.

11. The method of claim 1, wherein the effective amount of azelaic acid is 1 mM.

12. The method of claim 1, wherein the component of the plant is selected from the group consisting of leaves, roots, stems, fruits, flowers, and seeds.

13. The method of claim 1, wherein the composition is administered in combination with a plant nutrient.

14. The method of claim 1, wherein the ionic form of azelaic acid comprises sodium azelate or potassium azelate.

15. The method of claim 1, wherein the composition comprises a wetting agent.

16. The method of claim 1, wherein the composition further comprises an agent to induce a defense mechanism that depends on salicylic acid or ethylene or jasmonic acid or a combination thereof.

17. The method of claim 16, wherein the agent is selected from the group consisting of salicylic acid agonists, reactive oxygen species, benzothiazole, jasmonic acid, and ethylene or a derivative thereof.

18. The method of claim 1, wherein the azaelic acid is at least 75% purified.

19. The method of claim 1, wherein the plant is contacted in the presence of light.

* * * * *